US008552752B2

(12) United States Patent
Qiu

(10) Patent No.: US 8,552,752 B2
(45) Date of Patent: Oct. 8, 2013

(54) STRUCTURAL DETERMINATION APPARATUS AND METHOD

(75) Inventor: Changua Qiu, Manchester (GB)

(73) Assignee: Industrial Tomography Systems PLC, Manchester (GB)

(*) Notice: Subject to any disclaimer, the term of this patent is extended or adjusted under 35 U.S.C. 154(b) by 399 days.

(21) Appl. No.: 13/002,176

(22) PCT Filed: Jun. 18, 2009

(86) PCT No.: PCT/GB2009/001534
§ 371 (c)(1),
(2), (4) Date: Dec. 30, 2010

(87) PCT Pub. No.: WO2010/001089
PCT Pub. Date: Jan. 7, 2010

(65) Prior Publication Data
US 2011/0234246 A1 Sep. 29, 2011

(30) Foreign Application Priority Data
Jul. 1, 2008 (GB) .................................. 0812022.2

(51) Int. Cl.
G01R 27/08 (2006.01)

(52) U.S. Cl.
USPC .......................... 324/693; 324/71.1; 324/658

(58) Field of Classification Search
USPC ......................................... 324/658, 693, 71.1
See application file for complete search history.

(56) References Cited

U.S. PATENT DOCUMENTS

| 3,189,268 A * | 6/1965 | Nilsson ........................... 494/10 |
| 6,101,873 A | 8/2000 | Kawakatsu |
| 2006/0021432 A1 | 2/2006 | Salzmann |

OTHER PUBLICATIONS

Schlaberg, H. Inaki, et al., "Electrical Resistance Tomography for Suspended Sediment Measurements in Open Channel Flows Using a Novel Sensor Design", Particle & Particle Systems Characterization, Oct. 23, 2006, pp. 313-320, vol. 23, No. 3-4, Wiley-VCH.
Ricard, F. et al., "Monitoring of Multiphase Pharmaceutical Processes Using Electrical Resistance Tomography", Chemical Engineering Research and Design, Part A, Jul. 1, 2005, pp. 794-805, vol. 83, No. 7, Institution of Chemical Engineers.
Bolton, G.T., et al., "Development of an electrical tomographic system for operation in a remote, acidic and radioactive environment", Chemical Engineering Journal, May 10, 2007, pp. 165-169, vol. 130, No. 2-3, Elsevier Sequoia, Lausanne, CH.
International Search Report, Nov. 18, 2009, in related PCT Application No. GB2009/001534.
Written Opinion of the International Searching Authority, Nov. 18, 2009, in related PCT Application No. GB2009/001534.

* cited by examiner

Primary Examiner — Vincent Q Nguyen
(74) Attorney, Agent, or Firm — Jeffer Mangels; Butler & Mitchell LLP

(57) ABSTRACT

According to a first aspect of the invention there is provided apparatus arranged to determine an interface between two components that includes a reference electrode arranged to be connected to a constant voltage supply or ground; a measurement electrode, and a field generating device arranged to establish an electric field in at least one of the components; wherein the field generating device is configured to establish the electric field across the measurement electrode, and the apparatus is configured to measure a potential difference between the measurement electrode and the reference electrode, the potential difference between the measurement electrode and the reference electrode being indicative of the interface between the components.

29 Claims, 3 Drawing Sheets

STRUCTURAL DETERMINATION APPARATUS AND METHOD

The present invention relates to an apparatus arranged to determine an interface between two components and to a method of determining an interface between two components.

It is often useful to determine the position of an interface between two components, for example oil and water. In the case of an oil refinery, a crude oil mixture extracted from an oil deposit is often passed through a processing stage to remove undesirable contaminants. The processing stage may be used to separate the crude oil from any residual water or particulate contaminants in the mixture. The extracted crude oil is then passed into a processing chamber. When in the processing chamber, water, being less dense than oil, floats to the surface. Particulate contaminants fall to the bottom of the chamber. When the mixture has separated, the water is skimmed off the crude oil, and the particulate contaminants are extracted from the bottom of the chamber. It is important to know the positions of the interfaces between the crude oil and the water, and the crude oil and the particulate contaminants. If the positions of the interfaces are not well known, the separation of crude oil from the mixture may be imprecise. For example, without knowing the positions of the interfaces, crude oil may be extracted at the same time as the particulate contaminants or water, therefore wasting the crude oil or requiring the resulting mixtures to be refined again. This is inefficient, and can be expensive.

Similar problems arise in the dredging industry, where it is desirable to know the level, or change in level of sediment accumulating in, for example, a shipping channel. If the level of sediment is not known accurately enough, the channel may be over dredged as a precautionary measure, or under dredged on the assumption that the level of sediment is acceptable.

There have been various attempts at creating an apparatus and method that is able to reliably detect an interface between two components. One example of such an attempt uses a plurality of electrodes disposed on a supporting structure, as shown in FIG. 1.

FIG. 1 shows a prior art device used to determine the position of an interface between two components. In this example, the two components are sand 1 and water 2. The device determines the position of an interface 4 between the water 2 and sediment formed by sand 1 which has settled at the bottom of the container 3.

The prior art device comprises a plurality of electrodes EA-EG disposed in a linear fashion along an elongate supporting structure 5. Each one of the electrodes EA-EG is connected to a processing device 6, which is provided with a voltmeter V.

In use, the supporting structure 5 is placed into the container 3, and into the sand 1 and water 2. The supporting structure 5 is positioned such that it is adjacent to or in contact with the base of the container 3. In order to identify the interface between the sand 1 and water 2, potential differences are applied between various electrodes EA-EG, while the potential between other electrodes EA-EG is measured. This process is described in more detail below.

A potential difference is applied between electrode EA and electrode ED. An electric field is established between the electrodes EA and ED. The exact nature of the field between the electrodes EA and ED is dependent upon what material (i.e. sand 1 and/or water 2) is present in the region in which the field is established. Once the field has been established between electrodes EA and ED, the potential difference across a part of this field is measured using electrodes positioned between electrodes EA and ED, in this case electrodes EB and EC. The potential difference between electrodes EB and EC is measured and recorded by the processing device 6 and voltmeter V.

In the next step of the process, a potential difference is established between electrodes EB and EE. The potential difference applied between electrodes EB and EE is the same as that established between electrodes EA and ED in the previous step of the process. Thus, an electrical field is established in a different part of the sand 1 and water 2. Electrodes EC and ED disposed between electrodes EB and EE are used to measure the potential difference in a part of the field established between the electrodes EB and EE. As in the first step of the process, the potential difference between the electrodes EC and ED is measured and recorded by the processing device 6 and voltmeter V. This process is repeated using other electrodes until the magnitude of the potential difference between electrodes EE and EF has been measured and recorded.

By measuring the potential difference in parts of the sand 1 and water 2 in a linear fashion (i.e. from the bottom to the top of the container 3) a profile of the potentials can be established. From this profile of potentials, it is possible to determine the location of the interface between the sand 1 and water 2. For example, the potential measure between electrodes EC and ED will be different to that measured between electrodes EB and EC. This is because the space between electrodes EB and EC is filled with sand 1 and water 2 (i.e. an interface 4 is present), whereas the space between electrodes EC and ED is filled with only water 2. Therefore, a change in the measured potential will correspond to a change in material filling the space between adjacent electrodes, which can therefore lead to the determination of an interface 4 between, in this case, sand 1 and water 2.

While the above-mentioned prior art device and method is able to determine the interface between two components, e.g. sand 1 and water 2, the apparatus and method has disadvantages. For example, it can be seen from FIG. 1 and the description thereof that potential differences in the sand 1 and water 2 are measured between two adjacent electrodes, the potentials of which are floating, i.e. the potentials of each electrode may change. This can be problematic. It is conceivable that conditions between the adjacent electrodes do not change, whereas conditions at the electrodes may change. If the potentials of the electrodes do change, this will affect the measurement of the potential between the two electrodes, and may give a false representation of the structural properties between the two electrodes. Furthermore, the potential is not being measured at a specific point, but rather between two adjacent points. Thus the accuracy of the measurement may be dependent upon the spacing between adjacent electrodes. Therefore, in order to accurately determine the interface between two components, a large number of small electrodes may be necessary. This may be impractical, requiring a large number of connections to the processing device 6 and voltmeter V.

It is an object of the present invention to obviate or mitigate at least one of the above-mentioned disadvantages.

According to a first aspect of the present invention there is provided apparatus arranged to determine an interface between two components, comprising: a reference electrode arranged to be connected to a constant voltage supply or ground; a measurement electrode, and a field generating device arranged to establish an electric field in at least one of the components; wherein the field generating device is configured to establish the electric field across the measurement electrode, and the apparatus is configured to measure a potential difference between the measurement electrode and the reference electrode, the potential difference between the measurement electrode and the reference electrode being indicative of the interface between the components.

The apparatus may further comprise a plurality of reference electrodes, wherein each reference electrode is arranged to be connected to a constant voltage supply or ground. Each reference electrode may be arranged to be connected to a constant voltage supply of the same constant value or ground.

The field generating device may comprise the reference electrode and a first secondary electrode. The measurement electrode may be located in-between the reference electrode and the first secondary electrode.

The field generating device may comprise a first secondary electrode and a second secondary electrode. The measurement electrode may be located in-between the first secondary electrode and the second secondary electrode The apparatus may further comprise a plurality of measurement electrodes.

The secondary electrodes may be measurement electrodes.

The electrodes may be arranged to form a linear one-dimensional array of electrodes. The apparatus may further comprise a plurality of one-dimensional arrays.

The electrodes may be located on a supporting structure.

The apparatus may comprise a plurality of measurement electrodes, the effective resistance of each measurement electrode being different. The plurality of measurement electrodes may be arranged to form a linear one-dimensional array of measurement electrodes, and wherein the effective resistance of the electrodes increases along the array. The plurality of measurement electrodes may be arranged to form a linear one-dimensional array of measurement electrodes, the effective resistance of the electrodes in the array being substantially the same, and wherein the apparatus comprises a plurality of the linear one-dimensional arrays of electrodes, the electrodes in each array being configured to have a different effective resistance for each array, and the arrays being arranged in order of the effective resistance of the electrodes of the arrays. For instance, a plurality of rows (e.g. one-dimensional arrays) of electrodes may be provided, the electrodes within a row having the same effective resistance, that effective resistance being different for each row. The effective resistance may increase or decrease along the order in which the rows are arranged. In order to have a different effective resistance, the electrodes (e.g. within the same array, or in different arrays, depending on the embodiment) may have a different size, a different surface area, be formed from a different material, or be in connection with a resistor of a different magnitude.

According to a second aspect of the present invention there is provided a method of determining an interface between two components, comprising: maintaining a reference electrode at a constant electric potential; establishing an electric field in at least one of the components; measuring a potential difference between the reference electrode and a measurement electrode positioned in the electric field, and determining a property indicative of the interface from the potential difference between the reference electrode and the measurement electrode.

A potential difference may be measured between the measurement electrode and a plurality of reference electrodes, each reference electrode being maintained at a constant electric potential. Each of the reference electrodes may be maintained at the same electric potential.

The reference electrodes may be maintained at ground.

The method may further comprise measuring a potential difference between the reference electrode and the measurement electrode at a plurality of points within the electric field.

A plurality of measurement electrodes may be used to determine the potential at a plurality of points in the electric field.

A profile of potentials within the electric field may be established. The interface between the two components may be determined from changes in the profile.

The interface may be determined by a change in potential at the measurement electrode.

The interface may be determined from a change in potential at the measurement electrode due to a change in the coverage of the surface area of the measurement electrode by one of the components defining the interface.

The electric field may be established between a first secondary electrode, and the reference electrode. The electric field may be established between a first secondary electrode and a second secondary electrode. The secondary electrode may also be a measurement electrode.

By measuring the potential at a point within the components relative to an electrode maintained at a fixed potential, various disadvantages of prior art devices and methods are obviated or mitigated. For example, by measuring the potential relative to a fixed reference, the potential at a point is measured, as opposed to the potential between two points. This can lead to a more accurate measurement. Similarly, by measuring the potential between an electrode and a fixed reference, varying conditions at the electrode can be taken advantage of, as opposed to being a hindrance in the above-mentioned prior art device and method. For example, varying conditions at the electrode can be used to more accurately determine the position of an interface between two components, as opposed to making the measurement less accurate and less reliable.

Embodiments of the present invention will now be described, by way of example only, with reference to the accompanying drawings, in which.

Figure 2:
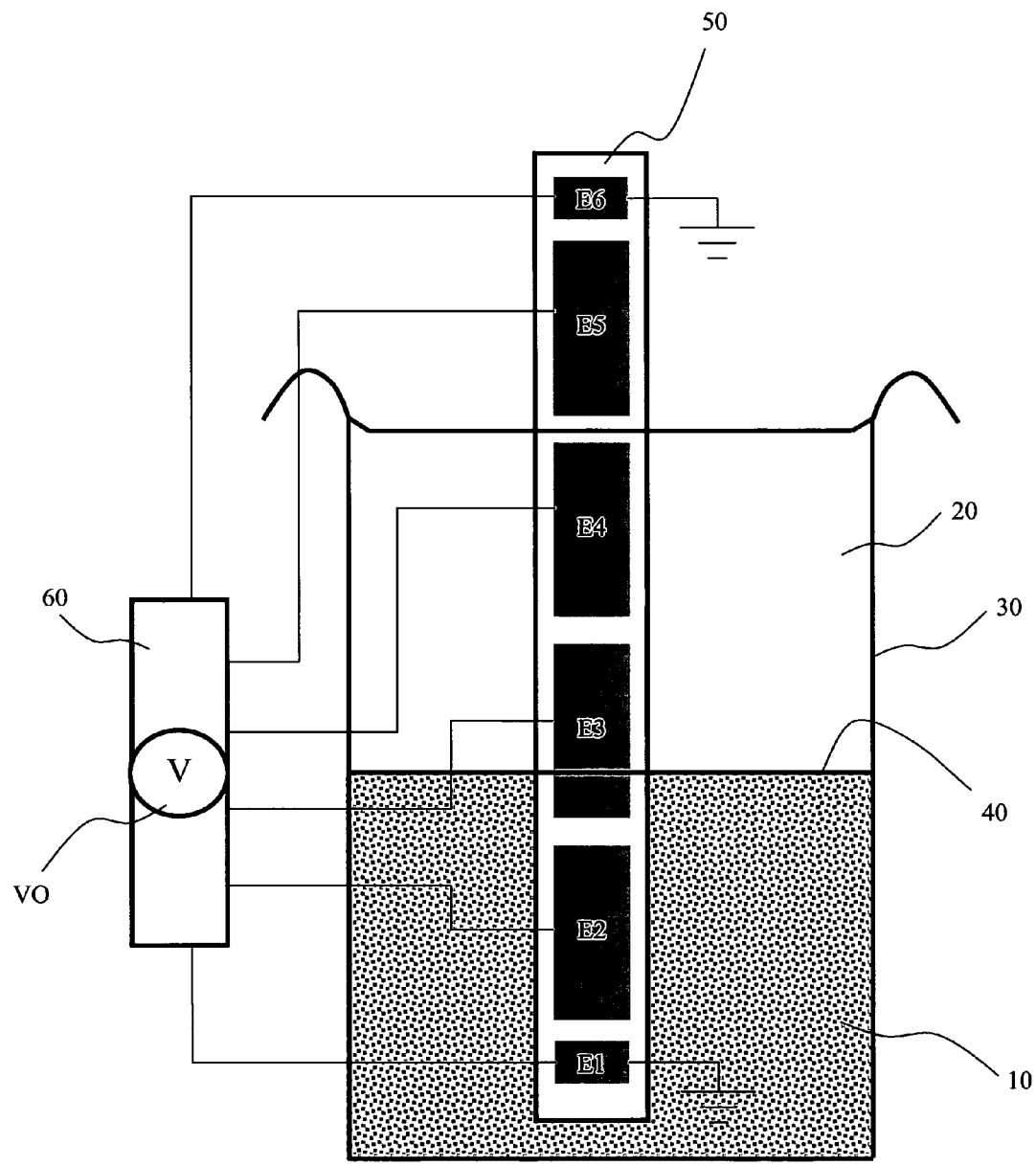
FIG. 2 depicts apparatus in accordance with an embodiment of the present invention.

FIG. 2 illustrates apparatus arranged to determine an interface between two components according to an embodiment of the present invention. In this particular case, the two components are sand 10 and water 20. The sand 10 and water 20 are located in a container 30. The sand 10 has fallen to the bottom of the container 30 and has therefore formed a sedimentary layer.

The apparatus arranged to determine the interface between the sand 10 and water 20 comprises a plurality of electrodes E1-E6 located in a linear fashion and attached to an elongate supporting structure 50. Each of the electrodes E1-E6 are connected to a processing device 60, which is itself provided with a voltmeter VO.

Figure 1:
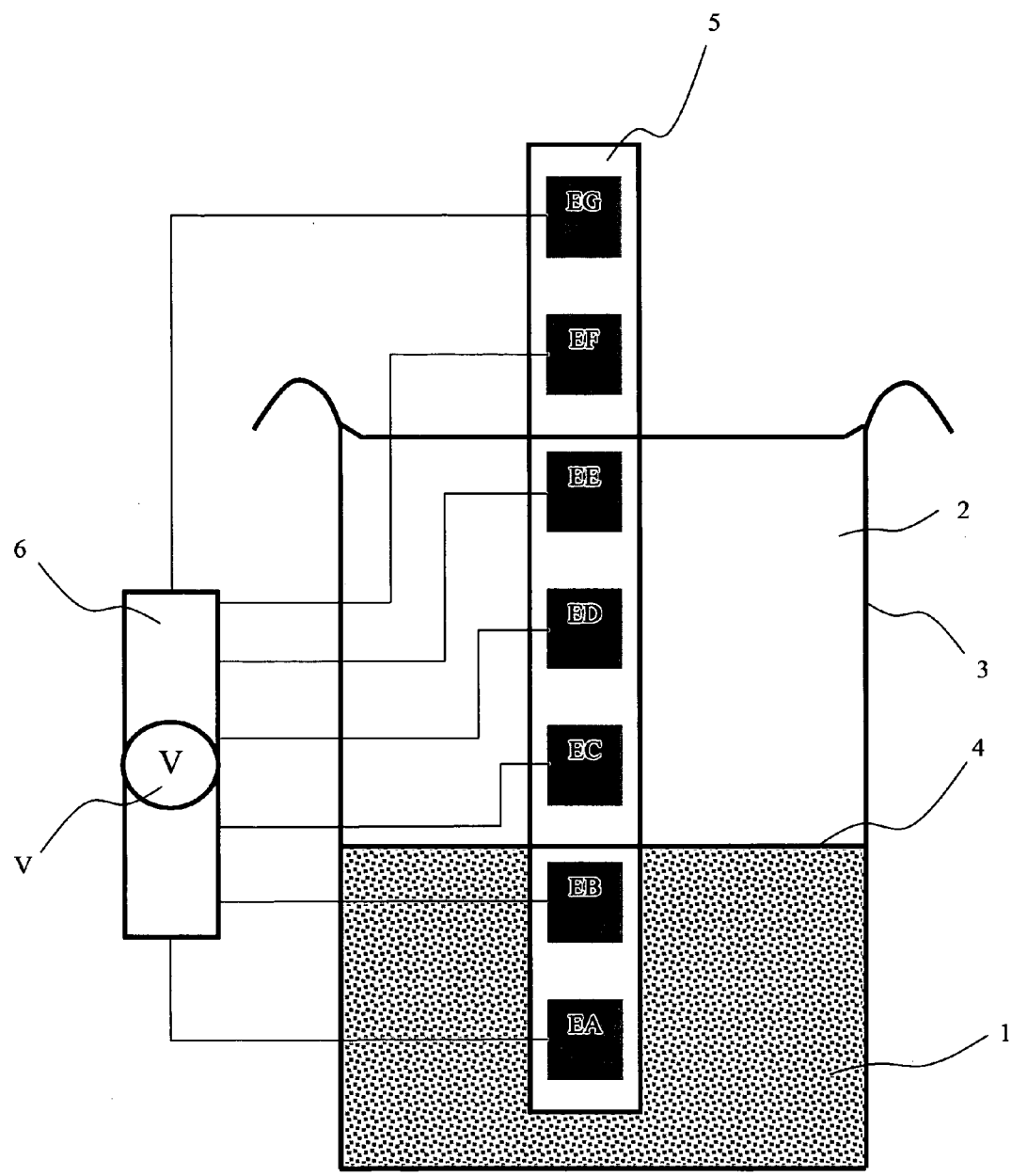
FIG. 1 depicts a prior art apparatus.

The main structural difference between the apparatus of the present invention (as shown in FIG. 2) and prior art apparatus (as shown in FIG. 1) is the provision of at least one electrode that is connected to a reference potential, in this case electrical ground. In the embodiment depicted in FIG. 2, the electrodes E1 and E6 at either end of the elongate supporting structure 50 are connected to electrical ground. The significance of the provision of at least one electrode connected to such a reference potential (e.g. electrical ground) will be explained in more detail below.

In use, the supporting structure 50 to which the electrodes E1-E6 are attached is placed into the container 30 in such a way that the supporting structure 50 extends through the water 20 and into the sand 10. In FIG. 2, the supporting structure 50 is adjacent to (and more or less in contact with) the base of the container 30. By positioning the supporting structure 50 and the electrodes E1-E6 attached thereto in this way, a linear profile of measured potentials in the sand 10 and water 20 can be determined.

An electric field is established in the sand 10 by establishing a potential difference between electrode E3 and electrode E1. In this process step, electrode E2 is a measurement electrode, whereas electrode E3 is a secondary electrode used to establish the electric field. It should be noted that electrode E1 is connected to electrical ground, and therefore the potential difference between the electrodes E1 and E3 is established by keeping electrode E3 at the desired potential using the processing device 60. While this potential is maintained, the potential at a point between electrodes E1 and E3 is measured using the electrode E2 (which is positioned between electrodes E3 and E1) in conjunction with the electrode E1. The potential of electrode E2 is measured relative to electrode E1, and recorded using the processing device 60 and the voltmeter VO. It can be seen that the potential of the sand 10 is measured at a specific point, as opposed to the prior art measurement described above, where the potential is measured across a part of the at least one of the two components.

In the next processing step, a potential difference is applied between electrodes E4 and E2, establishing an electric field there between. The potential difference between electrodes E2 and E4 is the same as that applied between electrodes E1 and E3 in the previous process step. Preferably, electrode E2 is grounded and the desired potential applied to electrode E4, such that the absolute values of the applied potentials are the same in each process step, as opposed to only the potential differences being the same. The potential difference at a point between the electrodes E2 and E4 is determined by measuring the potential of the electrode E3 (which is positioned between electrodes E2 and E4) relative to ground (i.e. electrode E1). Therefore, in this process step, electrode E3 is a measurement electrode, whereas electrodes E2 and E4 are secondary electrodes used to establish the electric field. It will be appreciated that measurement of the potential of electrode E3 will reveal the potential at a position in the two components of sand 10 and water 20 at a different location to that obtained in the previous processing step. The process is continued by grounding electrode E3, applying a potential to electrode E5 and measuring the potential at electrode E4 relative to ground. By doing this, a profile of the potentials in the sand 10 and water 20 can be established. By obtaining the profile of the potentials, a profile of the distribution of the sand 10 and water 20 can be determined, as will be described below.

FIG. 2 shows two grounded electrodes, E1 and E6. As described above, the potential at each point in the sand 10 and water 20 is measured relative to the grounded electrode E1. In order to ensure the measurement is as accurate and reliable as possible, potentials may also be measured relative to another grounded electrode, i.e. electrode E6. Measurement of potential relative to grounded electrode E6 can be made immediately after the potential has been measured relative to grounded electrode E1. This process if repeated for each measurement electrode. Alternatively, a profile of potentials can be obtained relative to grounded electrode E1, followed by a profile of potentials measured relative to the grounded electrode i.e. E6.

The potential at each point within the sand 10 and water 20 will vary depending on the distribution of the sand 10 and water 20 in the container 30. For example, a potential measured at electrode E2 (which is covered in sand 10) will be different to that measured at electrode E4 (which is surrounded by water 20). Thus, by observing changes in the measured potentials, a profile of the distribution of the sand 10 and water 20 can be determined, i.e. the location of the interface 40 between the sand 10 and water 20 can be determined.

By measuring the potential at the electrodes relative to a fixed reference value, for example electrical ground, the measurement obtained is more accurate than could otherwise be obtained by using two floating electrodes, the potentials of which are dependent on properties of the sand 10 and water 20. In addition, since measurements are taken relative to a fixed reference, the potentials of the electrodes are measured at the points at which the electrodes are located in the sand 10 and water 20, thereby allowing the potential at a specific point in the sand 10 and water 20 to be more accurately determined.

Figure 3:
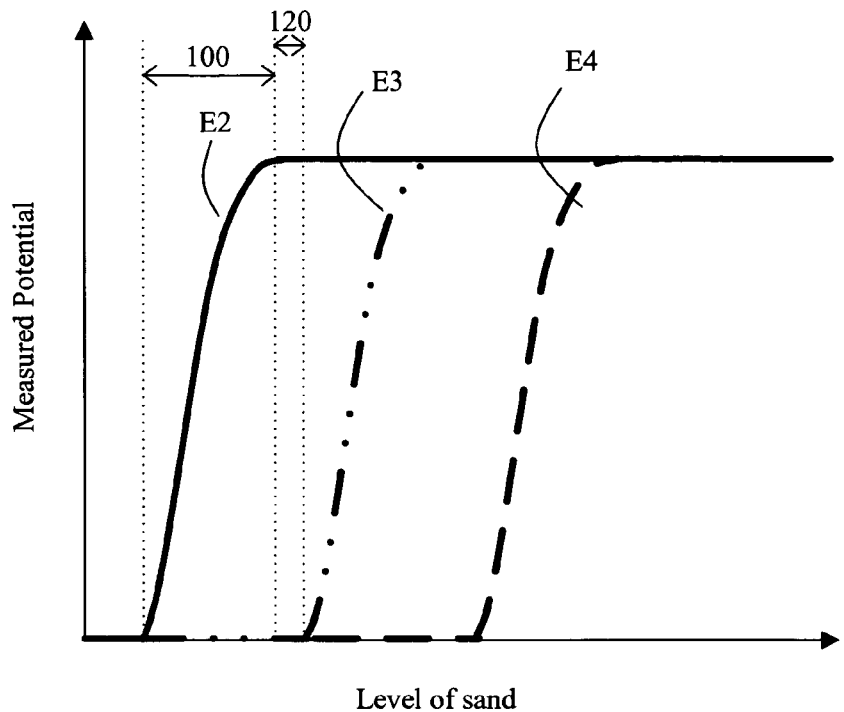
FIG. 3 depicts an operating principle of an embodiment of the present invention.

FIG. 3 shows a graph of results obtained using the apparatus of FIG. 2. Three data series are shown, corresponding to the measured potential of electrodes E2, E3 and E4 relative to ground (i.e. electrode E1 or FIG. 2). At the point at which the data series corresponding to electrode E2 increases dramatically, the level of the sand 10 is such that it is in contact with the electrode E2. As the increase in the measured potential is dramatic, the point at which the sand comes into contact with the electrode E2 is readily detectable. When the level of the sand 10 exceeds the position of the electrode E2 relative to the base of the container 30, the measured potential of electrode E2 does not increase. As the depth of the sand 10 further increases, the potential measured at electrode E3 increases dramatically since the sand 10 comes into contact with the electrode E3. Similar effects can be seen in the measured potential of electrode E4. Thus, it can be seen that the level of sand 10, and thus the interface between the sand 10 and water 20, can be readily determined and monitored.

FIG. 3 illustrates two regions of interest, 100, 120. The first region of interest 100 defines a range of sand 10 levels over which the measured potential of electrode E2 increases. This change in measured potential corresponds to the sand 10 covering an increasing amount of the surface of the electrode E2. This can be used to accurately determine the level of sand 10 in the container 30. The other region of interest 120 shows no changes in the measured potential of electrode E2, or indeed the potential of any other electrode. This region of interest 120 corresponds to the situation where the level of sand is between electrode E2 and E3. The features of these regions of interest 100, 120 are present in the data series for electrodes E2 and E3, although the regions of interest for these data series are not shown in FIG. 3.

Figure 4:
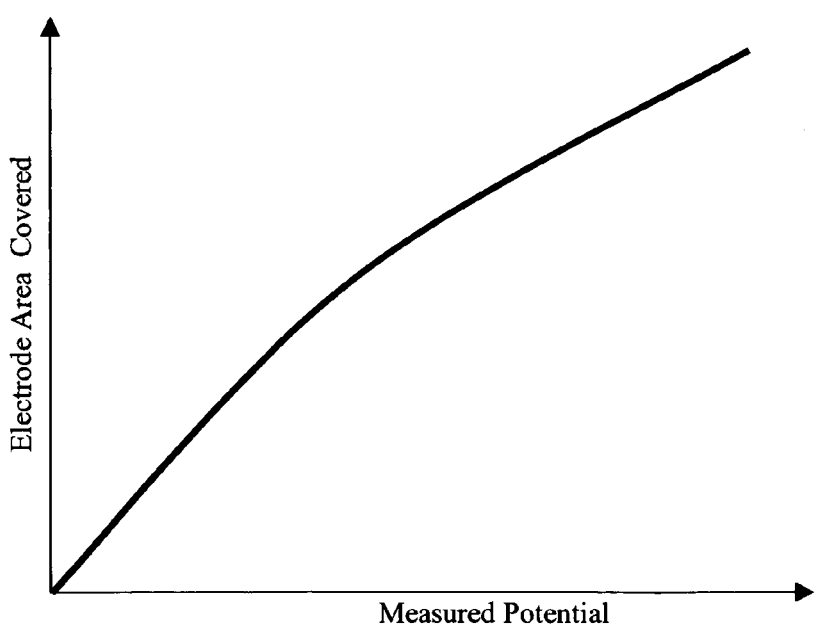
FIG. 4 depicts another operating principle of an embodiment of the present invention.

FIG. 4 is used to elaborate on region of interest 100 in FIG. 3. The graph of FIG. 4 shows how the measured potential of a given electrode increases when the surface area of the electrode is covered by sand 10. This is only possible because the potential is measured relative to a fixed value, for example electrical ground. In prior art devices, the electrodes are floating and it is not possible to easily determine whether a change in potential has been caused by a change in conditions at one of the electrodes, or by a change of conditions between the electrodes. By measuring the potential relative to ground (or any reference voltage), the embodiment of the invention provides a high resolution measurement of the level of sand 10 as it covers the electrode. In other words, the interface between the sand 10 and water 20 can be accurately determined and monitored.

It will be appreciated that the above embodiment has been described with reference to the use of electrodes that are grounded, for example the electrodes E1 and E6 of FIG. 2. However, it is not essential that the electrodes E1, E6 are grounded. Instead, the electrodes E1, E6 (or other electrodes) may be provided with a known fixed potential. For example, the potential of an electrode within the sand 10 and water 20 can be measured relative to an electrode maintained at a fixed potential of 3 volts. Electrical ground may be preferred since it is a convenient reference value. The embodiment described with reference to FIG. 2 has two grounded electrodes (i.e. electrodes E1 and E6 of FIG. 2) however, the potentials at which these electrodes are maintained can be different, so long as they are fixed.

If the electrodes E1 and E6 are to be fixed at non-zero reference values (even different non-zero reference values), this may have unwanted effects on the measurement of potential within the two components. For example, although the relative measured potentials will be unaltered (i.e. the changes will remain constant since the references are fixed), the absolute values of the potentials supplied will be different. This may have unwanted effects on the components, causing a reduction in the accuracy and reliability of the determination of the interface between the components.

As described above, since potentials of the electrodes are measured relative to a fixed reference value, a change in a measured potential at a given electrode can be used to determine a change in the level of sand relative to that electrode (e.g. the amount of sand covering the electrode). However, experimental results have indicated that as the length of the electrode increases, the resolution of any measurement obtained using this procedure tends to decrease. Therefore, the embodiment of the invention may be provided with a plurality of long electrodes, or a plurality of smaller electrodes which do not suffer a degradation in measurement resolution. Any suitable configuration of electrodes is possible. For example, the supporting structure 50 may be provided with a plurality of long electrodes and a plurality of shorter electrodes. The long and shorter electrodes may be interspersed with each other, or may be arranged in two parallel linear one-dimensional arrays. The long electrodes may be used to obtain a coarse and quick measurement of a level of sand 10 in the container 30, and then the relatively shorter electrodes may be used to obtain a slower but more accurate measurement of the level of sand 10. The exact dimensions of the electrodes may vary in accordance with the experimental. Similarly, the materials constituting the electrodes may be any suitable material.

The above-described embodiment has used electrodes on the supporting structure to establish electric fields in the two components. It will be appreciated that this is not essential, and that any field-generating device may be used. For example, an electric field may be generated using electrodes not part of the measurement apparatus.

The above-described embodiment has been shown to accurately determine the location of an interface between sand 10 and water 20. It is to be appreciated that the apparatus and method may be used to determine other interfaces, such as that between oil and water. The present invention is applicable to any situation where the potentials measured in two components can be distinguished. It will be further appreciated that the present invention may be used to determine more than one interface, for example interfaces present in a three or more component system. For example, the present invention may be used to determine the interface between oil and water, and also water and air.

The electrodes described above may be made from any suitable material. Preferably the material is resistance to corrosion. The material may be, for example, stainless steel, platinum, tantalum, or a metal alloy. The metal alloy may be a Hastelloy™ alloy. The alloy may be a highly corrosion resistant metal alloy. Such alloys are loosely grouped by the metallurgical industry under the material term "superalloys" or "high performance alloys".

The electrodes described above may be any suitable shape. For example, the electrodes may be rectangular or square in shape. A rectangular or square shaped electrode may make it easier to determine the amount of the electrode surface that is covered by a substance, for example sand, sediment or water, and thus the depth of the sand, sediment or water. This is because the coverage of such a rectangular or square shaped electrode will increase (substantially) linearly as the level of the substance covering the electrode changes. The electrodes described above may be any suitable size. For example, the electrode may have a length and/or width in the range of 5 mm to 50 mm.

The electrodes described above may have the same effective resistance. Alternatively, one or more electrodes may have a different effective resistance. For instance, the effective resistance of a number of electrodes arranged in a linear arrangement may decrease in a direction in which the number of electrodes extend. For example, the effective resistance may increase in a direction corresponding to an increasing depth of a substance in which the electrodes are immersed (or in other words the effective resistance may decrease in a direction corresponding to a decreasing depth of a substance in which the electrodes are immersed). The advantage of such an arrangement is that as the level of the substance (or substances) in which the electrodes are immersed increases, the signal (i.e. potential) of the electrode at the level of the substance (or interface between two substances) will be stronger (e.g. higher or less noisy), since the effective resistance of the electrode will be lower. The effective resistance of the electrodes may be changed by an appropriate change in the size of the electrode, the area of the electrode, the material of the electrode or the resistance between electrodes (for instance, controllable by including or changing the resistance between electrodes using resistors of different magnitudes). For example, in order to create a situation where the effective resistance varies in a linear manner along a number of electrodes, the size, area, or material of the electrodes, or the resistance between them, may be varied, for example, in a linear manner.

A plurality of electrodes may form a row. Electrodes in that row may have the same effective resistance. A plurality of rows may be provided, and arranged so that the rows for a stack of rows, for example arranged to extend in a direction parallel to an expected change in the level of a substance. Each row of electrodes may have a different effective resistance. For instance, the effective resistance of the electrodes of each row may increase or decrease in a direction parallel to an expected change in the level of a substance. The use a row of electrodes (rather than a single elongate electrode) may provide a better measurement resolution, since the potential of more than one electrode can be used to obtain properties of the substance in which the row is immersed, but in multiple positions (i.e. one for each electrode). The use of multiple rows allows the position of a substance level (or interface) to be determined. The difference in the effective resistance of the electrodes of each respective row is advantageous for the reasons given above.

It will be appreciated that the above embodiments have been described by way of example only. Various modifications may be made to the described embodiments, as well as to embodiments not described, without departing from the scope of the invention as defined by the claims that follow.

The invention claimed is:

1. Apparatus arranged to determine an interface between two components, comprising:
   a reference electrode arranged to be connected to a constant voltage supply or ground;
   a measurement electrode, and
   a field generating device arranged to establish an electric field in at least one of the components;
   wherein the field generating device is configured to establish the electric field across the measurement electrode, and the apparatus is configured to measure a potential difference between the measurement electrode and the reference electrode, the potential difference between the measurement electrode and the reference electrode being indicative of the interface between the components.

2. The apparatus as claimed in claim 1, further comprising a plurality of reference electrodes, wherein each reference electrode is arranged to be connected to a constant voltage supply or ground.

3. The apparatus as claimed in claim 2, wherein each reference electrode is arranged to be connected to a constant voltage supply of the same constant value or ground.

4. The apparatus as claimed in claim 1, wherein the field generating device comprises the reference electrode and a first secondary electrode.

5. The apparatus as claimed in claim 4, wherein the measurement electrode is located in-between the reference electrode and the first secondary electrode.

6. The apparatus as claimed in claim 4, wherein the secondary electrodes are measurement electrodes.

7. The apparatus as claimed in claim 1, wherein the field generating device comprises a first secondary electrode and a second secondary electrode.

8. The apparatus as claimed in claim 7, wherein the measurement electrode is located in-between the first secondary electrode and the second secondary electrode.

9. The apparatus as claimed in claim 1, further comprising a plurality of measurement electrodes.

10. The apparatus as claimed in claim 1, wherein the electrodes are arranged to form a linear one-dimensional array of electrodes.

11. The apparatus as claimed in claim 10, further comprising a plurality of one-dimensional arrays.

12. The apparatus as claimed in claim 1, wherein the electrodes are located on a supporting structure.

13. The apparatus as claimed in claim 1, wherein the apparatus comprises a plurality of measurement electrodes, the effective resistance of each measurement electrode being different.

14. The apparatus as claimed in claim 13, wherein the plurality of measurement electrodes are arranged to form a linear one-dimensional array of measurement electrodes, and wherein the effective resistance of the electrodes increases along the array.

15. The apparatus as claimed in claim 13, wherein the plurality of measurement electrodes are arranged to form a linear one-dimensional array of measurement electrodes, the effective resistance of the electrodes in the array being substantially the same, and wherein the apparatus comprises a plurality of the linear one-dimensional arrays of electrodes, the electrodes in each array being configured to have a different effective resistance for each array, and the arrays being arranged in order of the effective resistance of the electrodes of the arrays.

16. The apparatus as claimed in claim 13, wherein, in order to have a different effective resistance, the electrodes have a different size, a different surface area, are formed from a different material, or are in connection with a resistor of a different magnitude.

17. A method of determining an interface between two components, comprising:
    maintaining a reference electrode at a constant electric potential;
    establishing an electric field in at least one of the components;
    measuring a potential difference between the reference electrode and a measurement electrode positioned in the electric field, and
    determining a property indicative of the interface from the potential difference between the reference electrode and the measurement electrode.

18. The method as claimed in claim 17, wherein a potential difference is measured between the measurement electrode and a plurality of reference electrodes, each reference electrode being maintained at a constant electric potential.

19. The method as claimed in claim 18, wherein each of the reference electrodes are maintained at the same electric potential.

20. The method as claimed in claim 18, wherein the interface is determined by a change in potential at the measurement electrode.

21. The method as claimed in claim 18, wherein the interface is determined from a change in potential at the measurement electrode due to a change in the coverage of the surface area of the measurement electrode by one of the components defining the interface.

22. The method as claimed in claim 17, wherein the reference electrodes are maintained at ground.

23. The method as claimed in claim 17, further comprising measuring a potential difference between the reference electrode and the measurement electrode at a plurality of points within the electric field.

24. The method as claimed in claim 23, wherein a profile of potentials within the electric field is established.

25. The method as claimed in claim 24, wherein the interface between the two components is determined from changes in the profile.

26. The method as claimed in claim 17, wherein a plurality of measurement electrodes are used to determine the potential at a plurality of points in the electric field.

27. The method as claimed in claim 17, wherein the electric field is established between a first secondary electrode and the reference electrode.

28. The method as claimed in claim 27, wherein the secondary electrode is also a measurement electrode.

29. The method as claimed in claim 17, wherein the electric field is established between a first secondary electrode and a second secondary electrode.

* * * * *